United States Patent [19]

Kralovic

[11] Patent Number: 4,885,253
[45] Date of Patent: Dec. 5, 1989

[54] UNIVERSAL BIOLOGICAL INDICATOR SYSTEM

[75] Inventor: Raymond C. Kralovic, Austinburg, Ohio

[73] Assignee: Steris Corporation, Painesville, Ohio

[21] Appl. No.: 329,332

[22] Filed: Mar. 27, 1989

[51] Int. Cl.$^4$ ............................................. C12M 1/24
[52] U.S. Cl. ................................... 435/296; 435/294; 422/101
[58] Field of Search .................. 422/61, 101, 102; 435/294, 296

[56] References Cited

U.S. PATENT DOCUMENTS

| | | | |
|---|---|---|---|
| 3,661,717 | 5/1972 | Nelson | 195/103.5 |
| 4,345,028 | 8/1982 | Nelson et al. | 435/30 |
| 4,461,837 | 7/1984 | Karle et al. | 435/296 |
| 4,534,939 | 8/1985 | Smith et al. | 422/101 |
| 4,579,823 | 1/1986 | Ryder | 435/296 |
| 4,596,773 | 6/1986 | Wheeler | 435/31 |
| 4,743,537 | 5/1988 | McCormick | 435/296 |
| 4,810,651 | 3/1989 | Schwartz | 435/296 |

Primary Examiner—Carroll B. Dority
Attorney, Agent, or Firm—Fay, Sharpe, Beall, Fagan, Minnich & McKee

[57] ABSTRACT

A cylindrical, transparent capsule (10) is less than half filled with a liquid culture medium (12). An open end of the capsule is closed by supporting annulus (24) and a vent tube (28) having a vent aperture (30) at a free end thereof. The vent aperture is disposed at a volumetric center of the capsule such that an upper surface of the liquid culture medium is disposed below the vent aperture in any orientation of the capsule (FIG. 2). A heat labile membrane (32) which becomes porous in the presence of steam seals the vent passage but provided a pressure escape from the capsule at steam sterilizing temperatures. A disk inoculated with microorganisms is supported by the annular support. A cap (40) is slidably movable between a first position (FIG. 1) in which apertures (42) provide a liquid flow path between the inoculated disk and the exterior and a second position (FIG. 3) in which a severing ring (46) severs the support annulus bringing the inoculated disk and the culture medium into contact (FIG. 4).

20 Claims, 3 Drawing Sheets

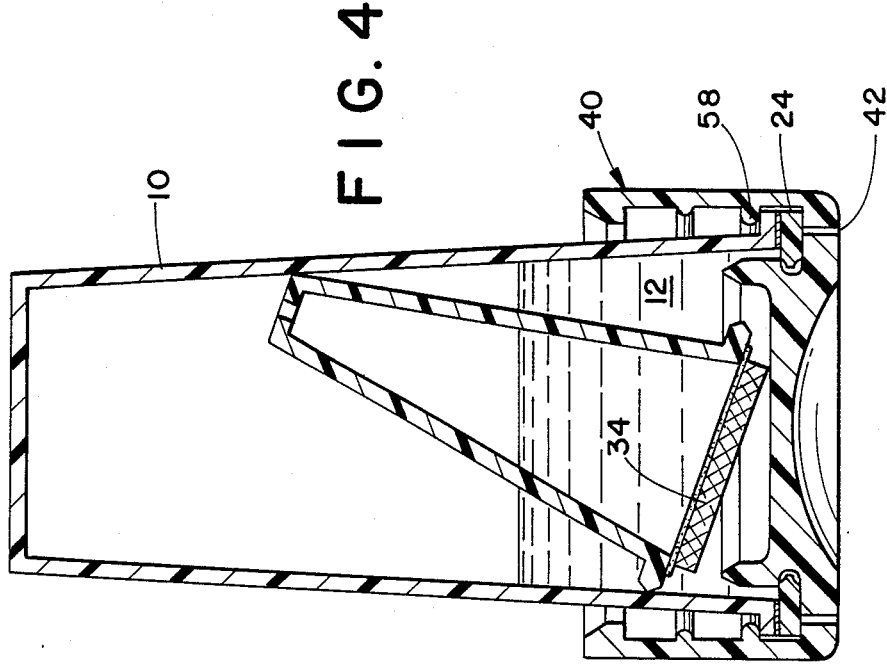
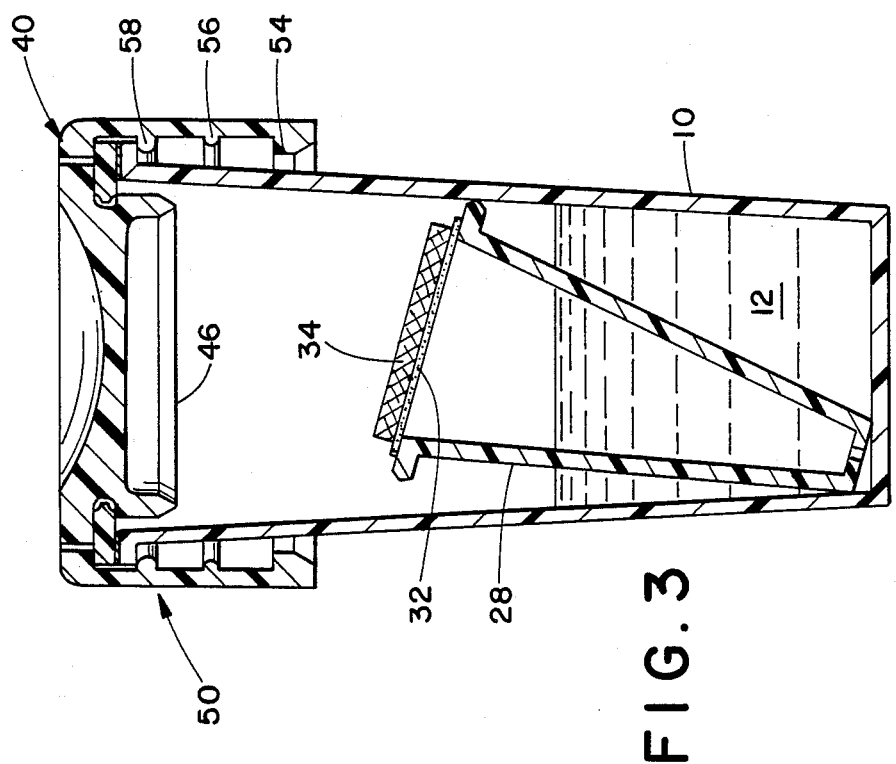

UNIVERSAL BIOLOGICAL INDICATOR SYSTEM

BACKGROUND OF THE INVENTION

The present invention relates to the art of biological indicator systems. It finds particular application in conjunction with indicating the completeness of a sterilization process and will be described with particular reference thereto.

Heretofore, various sterilization indicating systems have been provided. The systems generally included an element, e.g. a pad which was inoculated with a spore or other microorganism. The pad was mounted in a container and connected with the container exterior by a tortuous path. The container was disposed such that during a gas sterilization process, the pad was subject to substantially the same sterilizing conditions by gas that penetrates the tortuous path as the articles being sterilized. At the end of the sterilizing operation, the tortuous path was closed, a glass ampule containing a culture medium was fractured, and the pad and culture medium were brought together. After an appropriate incubation period, the culture medium was examined for evidence of growth of the inoculated microorganisms. A lack of microorganism growth was indicative of sterilization and growth of the microorganisms was indicative that the sterilization process was not complete. See for example U.S. Pat. Nos. 4,461,837 and 4,743,537.

One drawback of the prior art sterilization indicator systems was that they were limited to steam and gas sterilization processes. Liquids did not reliably penetrate the tortuous path or displace trapped air adjacent to the pad. Accordingly, they were unreliable as indicators of sterilization in a liquid sterilization process.

Another disadvantage of the prior art sterilization indicating systems was that they used a frangible glass ampule. The glass ampule was selected in order to withstand the internal pressure increase when the culture medium was heated to the temperature of sterilizing steam. However, the glass ampules had inherent drawbacks. For example, the glass acted as a heat sink, reducing the temperature to which an adjoining inoculated pad was subject. Also, glass ampules were subject to cracking at inappropriate times such as in transit or sudden changes in temperature. Yet, fracturing the glass ampule at the appropriate time was sometimes difficult.

The present invention provides a new and improved biological indicating system which is suitable for use in liquid sterilant systems, yet overcomes the above referenced problems.

SUMMARY OF THE INVENTION

In accordance with one aspect of the present invention, a biological indicator is provided. It has a first capsule which is less than half filled with a liquid culture medium. A vent tube extends from the exterior of the capsule to a vent aperture at a volumetric center of the capsule. In this manner, an upper surface of the culture medium is disposed below the vent aperture regardless of the orientation of the capsule. A thermolabile seal across the vent tube permits liquid and low temperature gaseous sterilants (e.g. ethylene oxide) to immerse the incubate pad without intermixing with the growth medium. The thermolabile seal will rupture in the presence of a high temperature sterilant (e.g. steam) and permit venting of the growth medium and thereby reduce pressure and permit use of an all plastic construction. A microorganism inoculated element is mounted on top of the thermolabile seal in the cap. A cap is slidably mounted on the capsule around the inoculated element for movement between first and second positions. The cap has apertures which provide both a liquid and gas flow path between the element and the exterior in the first position. The cap and capsule are sealed to block the passage of fluid along the flow path between the element and the exterior in the second position.

In accordance with another aspect of the present invention, the biological indicator includes a capsule that contains a liquid culture medium. The capsule has a closed first end and a frangible seal that seals an open second end. A cap is telescopically received on the capsule around the capsule second end for movement between first and second positions. A microorganism inoculated element is mounted in a volume defined between the cap and the capsule second end. The cap defines apertures which provide a liquid flow path between the element and the exterior in the first position. The cap includes a severing means which fractures the frangible seal as the cap moves from the first position to the second position such that the inoculated element and the liquid culture medium are permitted to come into contact. In the second position, the liquid flow path is sealed.

One advantage of the present invention is that it provides an indication of the effectiveness of a liquid sterilization process.

Another advantage of the present invention is that it is usable with liquid sterilants, low temperature gaseous sterilants, steam, penetrating radiation sterilization, plasma sterilization, and microwave sterilization. The only requirement being that the sterilizing medium be able to penetrate either a tortuous path or directly through the plastic.

Other advantages of the present invention reside in its ease of manufacture, shipping stability, cost effectiveness, and ease of operation.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts.

FIG. 3 is a cross sectional illustration of the biological indicator system of FIG. 1 in the closed or sealed position;

FIG. 4 is a cross sectional view of the biological indicator system of FIGURE in an inverted position to bring the inoculated element and culture medium into contact;

DETAILED DESCRIPTION OF THE PREFERRED EMBODIMENT

Figure 1:
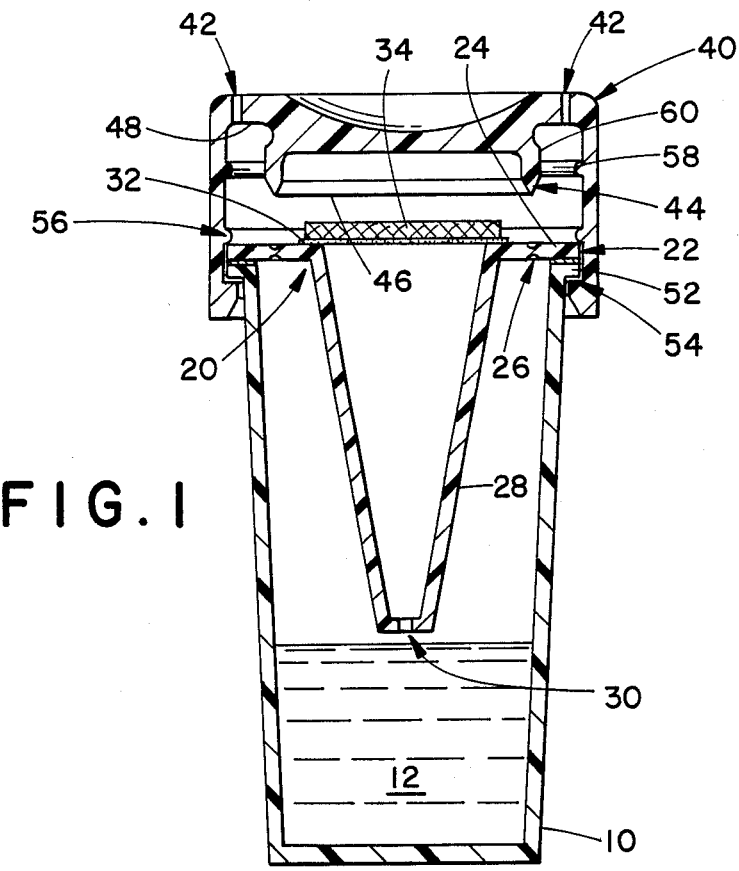
FIG. 1 is a cross sectional view of a biological indicator system in accordance with the present invention in an open or sterilant receiving position.

With reference to FIG. 1, the biological indicator system includes a transparent culture medium capsule 10. In the preferred embodiment, the capsule is a transparent plastic cylinder closed at a first bottom nd and open at a second or top end. Although the cylinder is illustrated as circular in cross section, rectangular, hexagonal, octagonal, and other cross sections are contemplated. A liquid culture medium 12 fills less than half of the total interior volume of the capsule. The actual volume of the cylinder is the interior volume of the cylinder per se less the volume displaced by any structures extending into the capsule interior.

Figure 2:
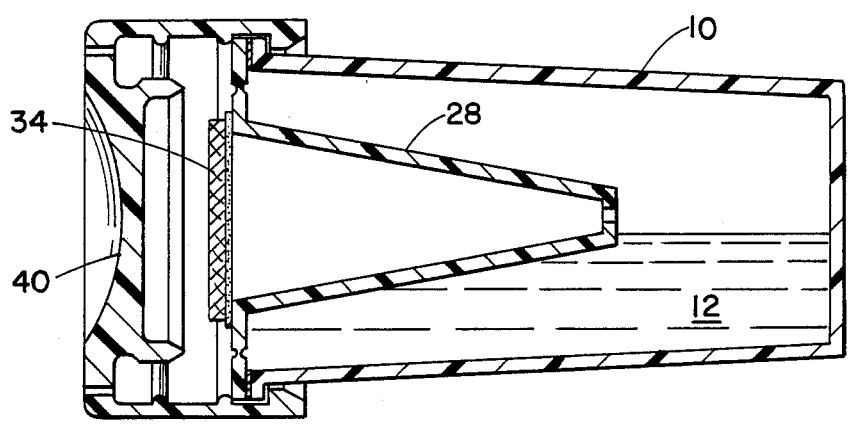
FIG. 2 is a cross sectional view of the biological indicator system of FIG. 1 in a tipped orientation.

A frangible sealing and supporting means 20 is heat sealed 22 across the opened end of the capsule 10. In the preferred embodiment, the frangible means includes an annulus 24 of resilient material that is connected by a weakened score line 26 to a vent tube 28. The vent tube 28 extends from the annulus to a vent aperture 30 disposed at or near the volumetric center of the capsule interior. The position of the vent aperture relative to the volumetric center and the amount of liquid culture medium 12 in the capsule are selected relative to each other such that an upper surface of the liquid culture medium remains below the vent aperture regardless of the orientation of the system (note FIG. 2). A vent sealing means 32 seals the vent aperture to prevent fluid communication between the liquid culture medium and the exterior of the capsule. In steam or other high temperature sterilization systems, the steam heats the liquid culture medium causing an interior pressure build-up within the capsule. To accommodate steam sterilizing, the sealing means 32 ruptures at a temperature below the boiling point of the medium and permits the venting of vapor gases from the interior of the capsule in the presence of steam. Various sealing means may be provided. In the preferred embodiment, the sealing means is a heat labile membrane or other thin polymeric film that fails or becomes vapor permeable at steam sterilization temperatures. Optionally, the sealing means may be a one way check or flap valve, a semi-porous membrane, or the like. Of course, if the biological indicator system is to be dedicated to liquid and low temperature gas sterilization, then the sealing means 32 need not vent the capsule interior at higher temperatures.

An microorganism inoculated disk or element 34 is supported by the supporting means 20. More specifically to the preferred embodiment, the inoculated disk is mounted on the heat labile membrane 32 which is mounted adjacent the supporting means. The inoculated disk is a pad or the like which has been inoculated with preselected microorganisms. Typically, the microorganisms are bacteria spores that have a resistance selected in accordance with the sterilizing procedure to be monitored. That is, microorganisms are selected which will be killed under more demanding sterilization conditions than bacteria or microorganisms on the items to be sterilized. Further, the microorganisms are also selected to have a relatively fast growth rate or short reproduction time in the liquid culture medium. In most applications, it is advantageous for the inoculated microorganisms to grow observably within a relatively short duration, e.g. 18 hours. Longer generation times will require a longer wait to determine whether the sterilization process has been successful. Various microbe inoculations and corresponding culture medium combinations are well known in the art.

A cap 40 is telescopically mounted on the second end of the capsule 10 for movement between a first position (FIG. 1) and a second or sealing position (FIG. 3). The cap surrounds the sealed opened end of the capsule to define an inoculated element receiving region or volume. A plurality of apertures 42 provide a liquid flow path for both liquids and gases from the exterior to the inoculated element receiving region. When the biological indicator system is placed along with items to be sterilized, the sterilant flows through the apertures contacting the inoculated element. The apertures provide sufficient flow such that the inoculated disk is subject to analogous sterilizing conditions as the items to be sterilized. The exact number, position, and diameter of the apertures may be selected in accordance with a particular sterilizing process. Preferably, the apertures are sufficiently large that they provide appropriate fluid flow rates in any orientation to be universal to substantially all sterilizing processes. A severing means 44 is mounted on the cap for severing the supporting means 20 to bring the inoculated element 34 into direct communication with the liquid culture medium 12. More specifically, the support severing means includes an annular projection 46 extending downward from an upper surface of the cap and having a diameter which is substantially the same as the weakened groove or score line 26. The annular projection has generally the same cross section as the capsule such that the supporting means is completely severed (FIG. 3) and the inoculated disk is urged downward toward the culture medium. The system is inverted (FIG. 4) to assure submersion of the inoculated element in the culture medium.

With reference to FIG. 3, the cap also includes a sealing means 48 for sealing the interior of the capsule and the biological indicator system from the exterior when the cap is in the second or closed position. In the preferred embodiment, the cap sealing means is a flat, annular surface adjacent the aperture which is urged into a sealing relationship with the annulus 24.

The detent means includes a ridge 52 at the top end of the capsule 10 and outer periphery of the annulus 22 which guides the telescopic sliding of the cap. A first cap projection 54 prevents decoupling of the cap and capsule. A second, annular cap projection 56 engages an upper surface of the ridge 52 for releasably holding the cap in the first position A third annular cap projection 58 engages a lower surface of the ridge 52 for releasably holding the cap in the second position A fourth annular ridge 62 on the severing means engages the free edge of the severed annulus to hold the cap in the second position. The second and third annular projections and the annulus free edge are dimensioned to permit ready sliding movement from the first position to the second. Optionally, the fourth ridge 60 and the annulus free severed edge can be configured to resist movement from the second position back to the first.

Figure 5:
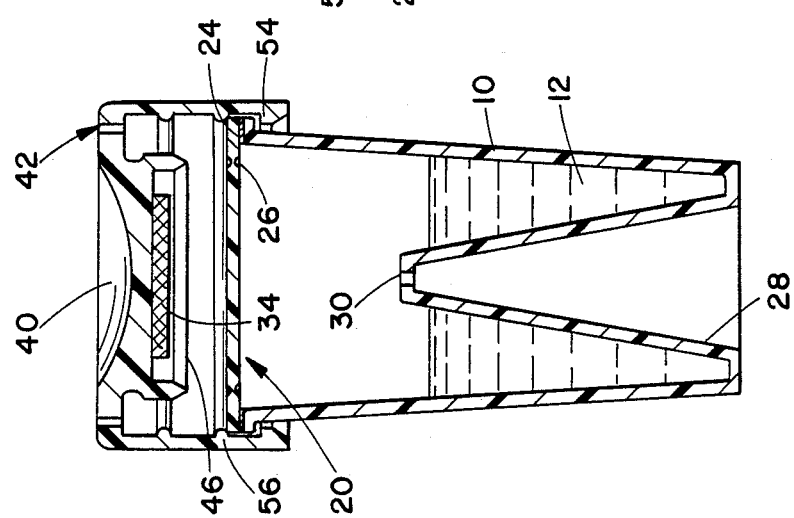
FIG. 5 is cross sectional view of an alternate embodiment of the present invention.

With reference to FIG. 5, the vent tube may extend from the vent aperture 30 to other walls of the capsule, e.g. the bottom wall.

Figure 6:
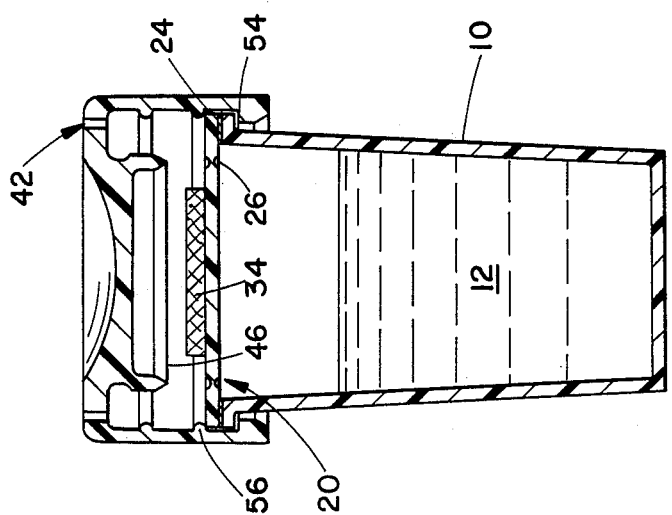
FIG. 6 is a cross sectional view of an alternate embodiment that is suited to low temperature sterilizing techniques; and, FIG. 7 is yet another alternate embodiment.

With reference to FIG. 6, the vent table and vent aperture may be deleted if the indicator system is limited to liquid and low temperature gas. The inoculated element 34 is mounted on the frangible supporting means 20 which supports it and seals it from the liquid culture medium 12. When severed by the severing means, the inoculated element can fall into the culture medium without shaking or inverting. Optionally, other venting or pressure relief structures may be provided. For example, the vent tube may pass from the volumetric center, along a side wall of the capsule, and through the annulus 24 which is covered by a heat sensitive seal. In this manner, the vent tube allows the inoculated element to fall into the liquid culture medium without inverting the system.

Figure 7:
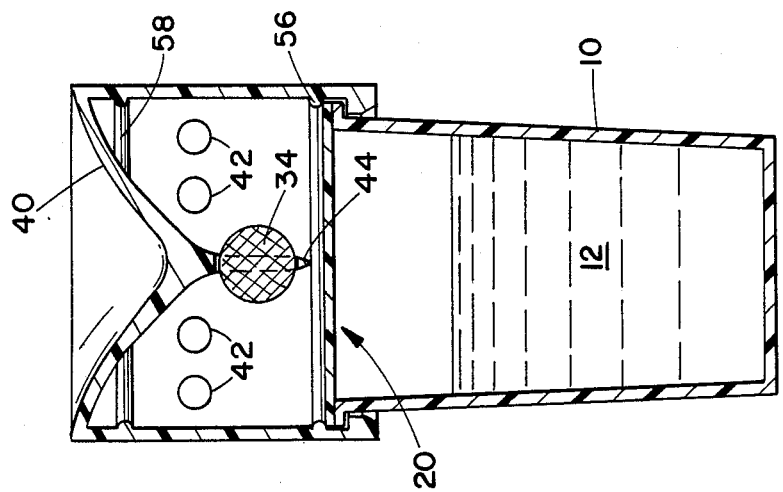

With reference to FIG. 7, the inoculated element 34 is mounted to the cap 40. Specifically, the inoculated element is mounted in a slot through a spike that functions as the severing means 44 in this embodiment. The spike punctures and rips the frangible means 20, e.g. a thin plastic sheet.

The invention has been described with reference to the preferred embodiment. Obviously, modifications and alterations will occur to others upon reading and understanding the preceding specification. For example, the second end capsule extends beyond the frangible means, the apertures 42 may be defined in the capsule to communicate between the inoculated element receiving region and the exterior of the system. It is intended that the invention be construed as including all such alterations and modifications insofar as they come within the scope of the appended claims or the equivalents thereof.

Having thus described the preferred embodiment, the invention is now claimed to be:

1. A biological indicator system comprising:
   a capsule whose interior volume is less than half filled with a liquid culture medium and which has a vent, tube extending from its exterior to a vent aperture in the tube at a volumetric center of the capsule interior volume such that an upper surface of the culture medium is disposed below the vent aperture regardless of the orientation of the capsule;
   a sealing means across the vent tube which permits gas to pass from the capsule interior volume to the exterior in the presence of steam and prevents communication with the capsule interior volume in the absence of steam;
   an element inoculated with microorganisms mounted adjacent the capsule;
   a cap movably mounted on the capsule surrounding the inoculated element for movement between at least first and second positions, the cap having apertures which provide a fluid flow path for both liquids and gas between the inoculated element and the exterior in the first position and which blocks the fluid flow path between the inoculated element and the exterior in the second position.

2. The system as set forth in claim 1 wherein the cap further includes a severing means for severing a structure around the inoculated element to provide fluid communication between the inoculated element and the liquid culture medium.

3. The system as set forth in claim 2 wherein the vent tube is mounted by an annular support means to one end of the capsule, the inoculated element being mounted on the annular support means, and the cap being mounted such that the severing means severs the annular support member from the capsule.

4. The system as set forth in claim 3 wherein the sealing means is a heat sensitive membrane which becomes porous to at least vapor in the presence of steam, the membrane being mounted to the annular support member peripherally around the vent tube.

5. The system as set forth in claim 3 wherein the capsule, the cap, and the vent tube are generally circular in cross section and are coaxial.

6. The system as set forth in claim 5 wherein the severing means is annular and coaxial with the capsule the cap and capsule being connected to undergo relative sliding movement parallel to a common axis.

7. The system as set forth in claim 2 wherein the capsule and the cap are both generally circular in cross section and have a common central axis and wherein the cap and capsule are mounted for relative sliding movement parallel to the common central axis.

8. The system as set forth in claim 7 wherein the severing means is generally annular and coaxial with the central axis.

9. The system as set forth in claim 8 wherein the inoculated element is mounted on a supporting means that extends generally transverse to the central axis and seals one end of the generally cylindrical capsule, the annular severing means contacting the supporting means peripherally around the inoculated element for severing the supporting means as the cap slides between the first and second positions.

10. The system as set forth in claim 9 wherein the vent tube is supported by the supporting means.

11. The system as set forth in claim 1 wherein the sealing means includes a heat labile member which becomes porous at least to gas in the presence of steam.

12. The system as set forth in claim 11 wherein the vent tube provides a fluid passage from the vent aperture to an interior of the cap, which vent passage is sealed by the heat labile membrane.

13. The system as set forth in claim 1 wherein the inoculated element is mounted to the cap.

14. A biological indicator system comprising:
   a capsule which is closed at a first end and open at a second end;
   a liquid culture medium disposed in the capsule;
   a frangible means extending across and sealing the capsule second end;
   a cap telescopically received over the capsule second end for movement at least between a first position and a second position, the cap and capsule second end defining an inoculated element receiving region;
   a microorganism inoculated element mounted in the inoculated element receiving region;
   a plurality of apertures in said cap for providing a liquid flow path between the inoculated element receiving region and an exterior of the cap in the first position and which liquid flow path is blocked in the second position;
   a severing means projecting from an interior of the cap toward the frangible means, the severing means being displaced from the frangible means in the first position and severing the frangible means as the cap moves from the first position to the second position.

15. The system as set forth in claim 14 further including a venting means for selectively venting an interior of the capsule to the exterior in the presence of steam.

16. The system as set forth in claim 15 wherein the venting means includes a vent tube which extends from the exterior to a vent aperture in the tube at a volumetric center of the capsule, the liquid culture medium filling less than one half of the capsule such that an upper surface of the culture medium is disposed below the vent aperture regardless of the orientation of the capsule.

17. The system as set forth in claim 16 further including a membrane which extends across and seals the vent tube, the membrane becoming porous at least to vapor in the presence of steam.

18. The system as set forth in claim 17 wherein the vent tube is supported by the frangible means.

19. The system as set forth in claim 16 wherein the cap and capsule are both circular and further including detent means for releasably holding the cap in the first and second positions.

20. The system as set forth in claim 14 wherein the capsule is constructed of a transparent plastic such that the inoculated element is visible through the transparent capsule in the second position.

* * * * *